United States Patent [19]
Dietrich

[11] Patent Number: 6,010,038
[45] Date of Patent: Jan. 4, 2000

[54] APPARATUS FOR THE VOLUMETRIC METERING OF SUBSTANCES AND USE OF THE APPARATUS

[75] Inventor: Frédéric Dietrich, Le Mont-Pelerin, Switzerland

[73] Assignee: Transpowder Ltd., Dublin, Ireland

[21] Appl. No.: 08/796,016

[22] Filed: Feb. 5, 1997

[30] Foreign Application Priority Data

Feb. 7, 1996 [DE] Germany .......................... 196 04 411

[51] Int. Cl.⁷ ................................................. B65D 88/54
[52] U.S. Cl. .................. 222/282; 222/152; 222/189.06; 222/306; 222/434; 222/438; 141/65
[58] Field of Search .............................. 222/152, 189.06, 222/282, 291, 306, 434, 438, 386; 141/65, 81, 129, 258–262

[56] References Cited

U.S. PATENT DOCUMENTS

| | | | |
|---|---|---|---|
| 2,540,059 | 1/1951 | Stirn et al. | 141/1 |
| 4,337,880 | 7/1982 | Rozmus | 222/152 |
| 4,671,430 | 6/1987 | Dinius | 222/135 |
| 5,797,435 | 8/1998 | Wada | 222/306 |

*Primary Examiner*—Robert M. Fetsuga
*Assistant Examiner*—Timothy L. Maust
*Attorney, Agent, or Firm*—Bachman & LaPointe, P.C.

[57] ABSTRACT

In an apparatus for the volumetric metering of fluid, pasty and/or powdery substances, in particular for separating small amounts of substance from a delivery flow, by means of an adjustable-volume measurement chamber which is connected to a feed conduit and which is provided with an outlet, a capillary measurement conduit (22) is connected as the measurement chamber to a vacuum conduit (33). In particular cases the measurement conduit can be acted upon by conveyor air, but in the normal case it is provided with a metering needle which is displaceable therein and whose free needle end (19) delimits the measurement chamber at one end. In addition a movable sealing body (56) is to be associated as a closure element with the mouth opening (23) of the measurement conduit (22), that serves as the outlet, which sealing body can be connected to a closure device (50) which is limitedly rotatable about a pivot means (52). The sealing body (56) is to be provided on an arm (51) of a closure flap (50) which is of a rocker-like configuration and whose other arm (48) is pivotably connected to a control member (44).

36 Claims, 2 Drawing Sheets

APPARATUS FOR THE VOLUMETRIC METERING OF SUBSTANCES AND USE OF THE APPARATUS

BACKGROUND OF THE INVENTION

The invention concerns an apparatus for the volumetric metering of fluid, pasty and/or powdery substances—in particular for separating small amounts of substance from a delivery flow—by means of an concerns uses of the apparatus.

In the industrial area the measured quantitative addition of amounts of substances is effected in various ways and always involves measurement, control and regulating procedures. Thus solid substances are generally metered in accordance with weight or numbers of items, liquid substances are metered using through-flow measuring devices or metering pumps on the basis of volume, and gaseous substances are metered with flowmeters.

Conventional apparatuses for metering fluid, pasty and powdery substances or agents are so designed that the operation of ascertaining the amount involved is effected in a comparatively complicated manner and with only relative accuracy. That applies in particular to metering installations for small amounts, as occur for example in the pharmaceutical or chemical industry; for the metering operation, it is a matter of crucial importance that the installations used can be easily and quickly cleaned, which however is possible only to a limited extent with the apparatuses available on the market. The known apparatuses also scarcely afford the required degree of constancy in terms of the amounts which are measured off or metered. Deviations—and therewith inaccurate amounts—frequently occur, for which reason the known metering apparatuses can give rise to problems in for example metering vaccination substances with a sufficient degree of accuracy; hitherto such substances have generally been metered into ampoules by hand.

In consideration of that state of the art, the inventor set himself the aim of providing an apparatus of the kind set forth in the opening part of this specification for the reliable metering of small to very small amounts of substance, in other words, increasing the reproducible metering accuracy therefor. The invention further seeks to provide for enlarging the area of use of metering apparatuses.

SUMMARY OF THE INVENTION

In accordance with the invention at least one capillary measurement conduit is connected as a measurement chamber to a vacuum conduit, which measurement conduit preferably accommodates a metering needle which is displaceable therein and the free needle end of which delimits the measurement chamber at one end. In the normal case the capillary measurement conduit will contain the metering needle, but in special cases the needle can be replaced by an air flow.

Advantageously a movable sealing body is associated as a closure element with the mouth opening of the measurement conduit, which opening serves as an outlet, the sealing body preferably being connected to a closure device. In accordance with the invention the latter is limitedly rotatable about a pivot means.

In accordance with a further feature of the invention the sealing body is carried on an arm of a closure flap which is of a rocker-like configuration and whose other arm is pivotably connected to a control member.

It has been found advantageous in terms of structure and operational reliability for the metering needle to be mounted with its end remote from the measurement conduit in a piston which is connected to a drive device and which axially movably extends in a cylindrical opening of a housing block containing the measurement conduit.

In accordance with the invention two side conduits extend away from the capillary measurement conduit—displaced laterally and in respect of height relative to each other—of which the side conduit adjacent the metering needle carries the flow of medium to the measurement carrier while that nearer the outlet is connected to a vacuum conduit. The latter is also to be associated with a filter device of the housing block.

Particularly for dealing with a plurality of components, it is desirable to provide in the apparatus a plurality of measurement chambers or measurement passages of a volume which is variable by a respective metering needle.

The preferred volume of the measurement chamber is specified at at most 1 cm$^3$ but preferably up to at most 5 mm$^3$, in particular 1 mm$^3$.

It is desirable for a plurality of measurement chambers or measurement conduits arranged in the apparatus to be provided with mutually different chamber volumes.

In order to permit uncomplicated operation, the closure device or closure flap is designed to be actuated under computer control and is designed to be moved into the closure and open position respectively mechanically or electromagnetically, pneumatically or hydraulically.

It is also possible for the closure devices or closure flaps of the plurality of measurement chambers or measurement conduits to be designed to be actuable individually, in groups or jointly.

The metering apparatus according to the invention and the structure associated therewith permit a high degree of accuracy in terms of metering effect, as is required for example for vaccination substances. The particular advantage of the invention is that a plurality of such apparatuses can be arranged in side-by-side relationship in order to permit automatic metering procedures for a mixture comprising a plurality of components; the components to be metered are metered in a plurality of measurement chambers arranged in a linear or circular configuration or a plurality of apparatuses each having a respective measurement chamber and are thereafter transferred into receiving containers by opening the outlets or the closure flap.

A matter of particular significance in terms of keeping the apparatus clean is the possibility of cleaning the side conduits of the measurement conduit in a counter-flow mode when the closure flap is in the closure position, that is to say with the measurement conduit closed.

This therefore provides an apparatus which attains the object intended by the inventor, for preferred use for the purposes of micro-metering in the pharmaceutical or chemical industry, in the foodstuffs industry, in the area of bio-engineering or in automated analysis procedures.

BRIEF DESCRIPTION OF THE DRAWINGS

Further advantages, features and details of the invention are apparent from the following description of preferred embodiments and with reference to the drawing in which.

DETAILED DESCRIPTION OF PREFERRED EMBODIMENTS

Figure 1:
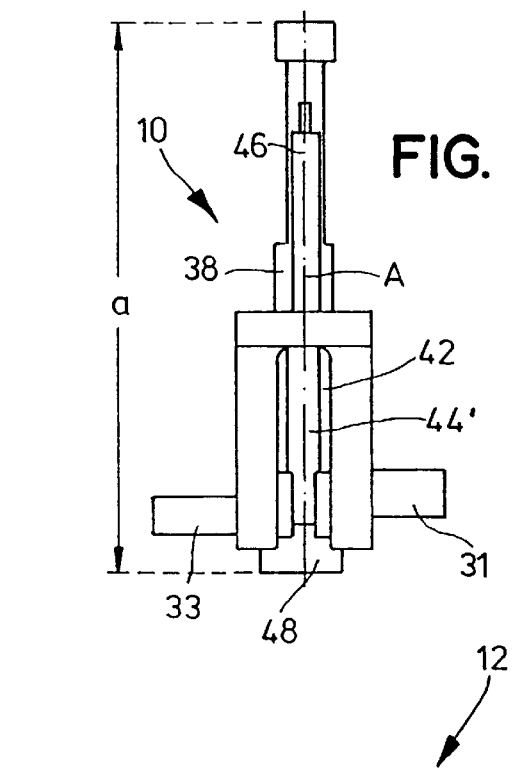
FIG. 1 shows a front view of a metering apparatus.

A metering apparatus 10 of a height a of about 110 mm has a cuboidal housing block 12 with a bore, extending on the longitudinal axis A thereof, as a cylinder chamber 14 for a piston 16 which can be raised and lowered therein. Axially projecting from the piston 16 is a metering needle 18 which is movable therewith. The diameter d of the cylinder chamber 14 is shorter than a third of the width b of about 30 mm of the housing block 12 whose height e is about 50 mm.

At a spacing h from the bottom surface 20 of the housing the cylinder chamber 14 passes with a conical end 15 into a capillary measurement conduit 22 as a measurement chamber; it is disposed on the longitudinal axis A and terminates in an outlet cavity 24 in the housing block 12.

Figure 3:
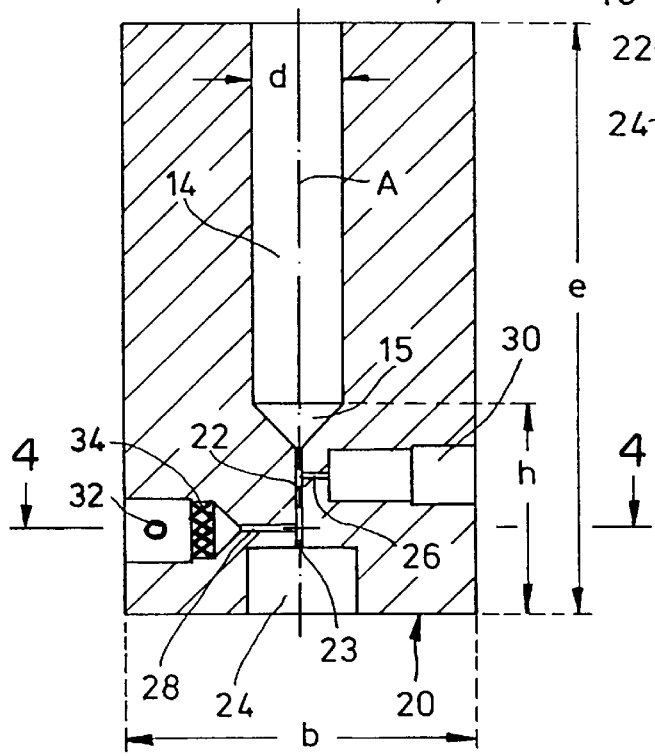
FIG. 3 is a front view of a part of FIG. 2.
Figure 4:
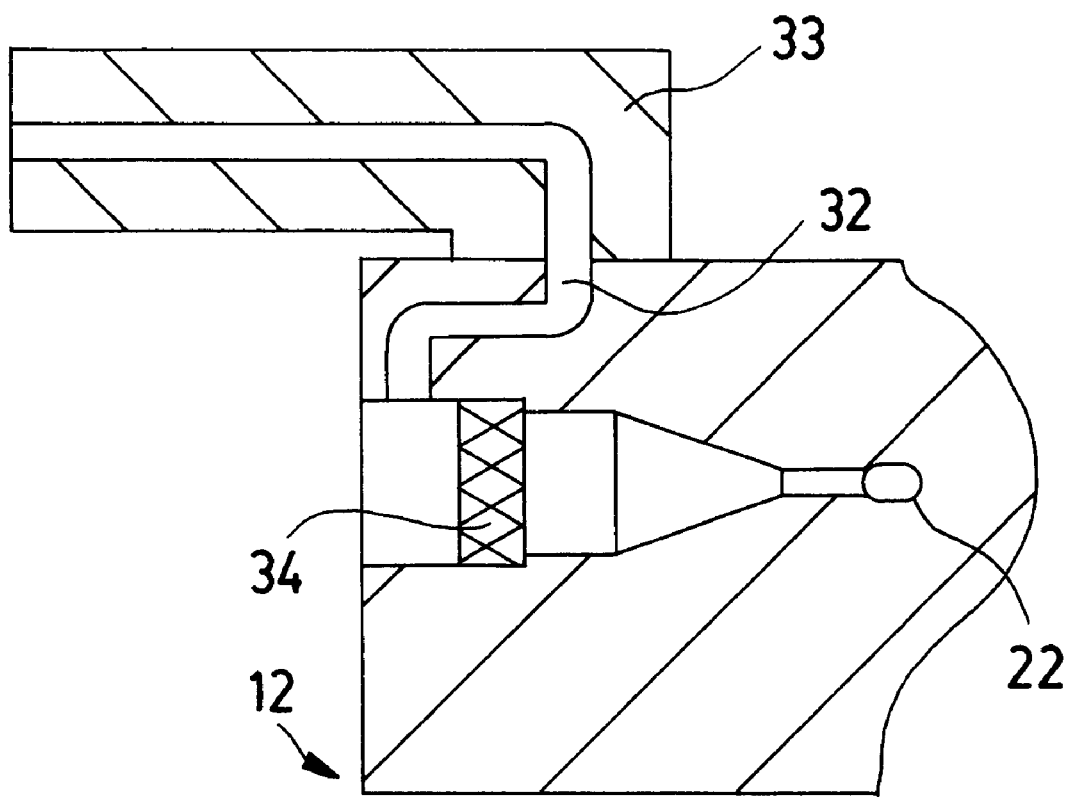
FIG. 4 is a partial sectional view taken along line 4—4 of FIG. 3.

Between the conical end 15 and the outlet cavity 24, two side conduits 26 and 28 which are also capillary conduits extend from the measurement conduit 22 at a right angle and in displaced relationship laterally and in respect of height. One of the side conduits 26 opens into an inlet chamber 30 at the right in FIG. 3 for a medium to be metered, while the other side conduit 28 opens into a vacuum connection chamber 32 with filter 34. The diameter of the conduits 22, 26, 28 is a fraction of the diameter d of the cylinder chamber 14.

In particular FIG. 1 clearly shows that a connecting member 31 is connected to the inlet chamber 30 and a vacuum conduit 33 is connected to the vacuum connection chamber 32.

The above-mentioned piston 16 is connected by way of a screw bolt 36 to a drive device indicated at 38 for the metering needle 18 which projects with its free needle end 19 into the above-mentioned measurement conduit 22, and the piston thus controls the stroke movement of the needle.

Figure 2:
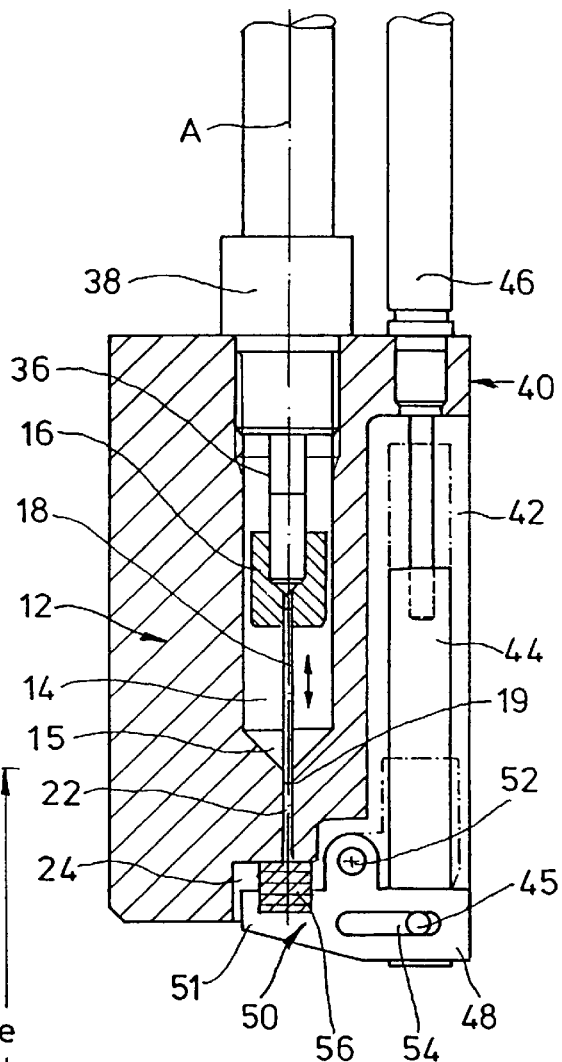
FIG. 2 is a view in longitudinal section on an enlarged scale through the metering apparatus.

Referring to FIG. 2 there can be seen therefrom at the center of the front surface 40 of the housing block 12 a recess 42 which is parallel to the axis of the housing block and in which a guide linkage 44 movably extends; it connects an actuating cylinder 46 to a free arm 48 of a closure flap 50 which is pivotably mounted on the housing block 12; the closure flap 50 is arranged in a rocker-like manner on the pivot 52 and its actuating arm 51 is variable in respect of its spacing relative to the mouth opening 23 of the measurement conduit 22. A slot 54 acting as a sliding guide for a transverse pin 45 of the guide linkage 44 can be seen beneath the pivot 52 on the free arm 48 of the closure flap 50.

The actuating arm 51 of the closure flap 50 carries a block-shaped sealing insert 56 which in the closure position shown in FIG. 2 rests in the outlet cavity 24 and in that position holds closed the mouth opening 23 of the measurement conduit 22.

The measurement section or the measurement volume of the measurement conduit 22 is delimited or adjusted in an upward direction by the metering needle 18 which is guided therein. When the measurement operation is being carried out, a reduced pressure is applied in the vacuum connection chamber 32 and at the filter 34 and the medium to be metered is sucked in by way of the inlet chamber 30. The filling time for the measurement chamber or the measurement conduit 22 is adjusted and controlled by an electronic control.

For the purposes of cleaning the side conduits 26, 28 they can be flushed through in a counter-flow mode when the closure flap 50 is closed.

Preferably a plurality of those metering apparatuses are used arranged in groups in a linear or annular configuration.

In an embodiment which is not shown, a single housing block 12 may contain a plurality of parallel measurement conduits 22 and therewith also a plurality of metering needles 18 together with drive 38 and a corresponding number of closure flaps 50; the metering needles 18 and the closure flaps 50 can be controllable jointly, individually or in selectable groups.

I claim:

1. Apparatus for the volumetric metering of fluid, pasty and/or powdery substances, in particular for separating small amounts of substance from a delivery flow, by means of an adjustable-volume measurement chamber which is connected to a feed conduit and which is provided with an outlet, wherein at least one capillary measurement conduit is connected as a measurement chamber to a vacuum conduit and two capillary side conduits extending laterally from the at least one capillary measurement conduit in a mutually displaced relationship laterally and in respect to height.

2. Use of the apparatus as set forth in claim 1 for the micro-metering of substances in the chemical or pharmaceutical industry.

3. Apparatus as set forth in claim 1 wherein one of said two capillary side conduits is connected to the feed conduit for the delivery flow.

4. Apparatus as set forth in claim 1 wherein volume of the measurement chamber is at most 1 $cm^3$.

5. Apparatus as set forth in claim 1 wherein the volume of the measurement chamber is at most 250 $mm^3$, preferably 50 $mm^3$.

6. Apparatus as set forth in claim 1 wherein the volume of the measurement chamber is up to at most 5 $mm^3$, preferably 1 $mm^3$.

7. Apparatus as set forth in claim 1 wherein provided in the capillary measurement conduit is a metering needle which is displaceable therein and whose free needle end delimits the measurement chamber at one end.

8. Apparatus as set forth in claim 7 wherein a movable sealing body is associated as a closure element with the mouth opening of the measurement conduit, which serves as an outlet.

9. Apparatus as set forth in claim 7 wherein the metering needle is supported with its end remote from the capillary measurement conduit in a piston which axially movably extends in a cylindrical opening in a housing block containing the measurement conduit.

10. Apparatus as set forth in claim 9 wherein the piston is connected to a drive device.

11. Apparatus as set forth in claim 9 wherein the volume of the measurement chamber is at most 1 $cm^3$.

12. Apparatus as set forth in claim 9 wherein the volume of the measurement chamber is up to at most 250 $mm^3$, preferably 50 $mm^3$.

13. Apparatus as set forth in claim 9 wherein the volume of the measurement chamber is up to at most 5 $mm^3$, preferably 1 $mm^3$.

14. Apparatus as set forth in claim 7 wherein arranged therein are a plurality of measurement chambers or measurement conduits each of a volume which is variable by a respective metering needle.

15. Apparatus as set forth in claim 14 wherein the measurement chambers or measurement conduits arranged therein are disposed in one or more rows.

16. Apparatus as set forth in claim 14 wherein the measurement chambers or measurement conduits arranged therein are disposed in an annular configuration in one or more circles.

17. Apparatus as set forth in claim 14 wherein a plurality of measurement chambers or measurement conduits which are arranged in the apparatus have mutually different chamber volumes.

18. Apparatus as set forth in claim 14 wherein the closure devices or closure flaps of the plurality of measurement chambers or measurement conduits are adapted to be individually controllable.

19. Apparatus as set forth in claim 14 wherein the closure devices or closure flaps of the plurality of measurement chambers or measurement conduits are adapted to be controllable in groups.

20. Apparatus as set forth in claim 14 wherein the closure devices or closure flaps of the plurality of measurement chambers or measurement conduits are adapted to be jointly controllable.

21. Apparatus as set forth in claim 1 wherein a movable sealing body (56) is associated as a closure element with the mouth opening of the measurement conduit, which serves as an outlet.

22. Apparatus as set forth in claim 21 wherein the sealing body is connected to a closure device and the latter is limitedly rotatable about a pivot means.

23. Apparatus as set forth in claim 21 wherein the sealing body is provided on an arm of a closure flap.

24. Apparatus as set forth in claim 23 wherein said apparatus has a plurality of measurement chambers each with a closure flap wherein the closure flaps of the plurality of measurement chambers are adapted to be individually controllable.

25. Apparatus as set forth in claim 23 wherein said apparatus has a plurality of measurement chambers each with a closure flap wherein the closure flaps of the plurality of measurement chambers are adapted to be controllable in groups.

26. Apparatus as set forth in claim 23 wherein said apparatus has a plurality of measurement chambers each with a closure flap wherein the closure flaps of the plurality of measurement chambers are adapted to be jointly controllable.

27. Apparatus as set forth in claim 23 wherein the closure flap is adapted to be actuable under computer control.

28. Apparatus as set forth in claim 27 wherein the closure flap is adapted to be moved into the closure or open position mechanically or electromagnetically.

29. Apparatus as set forth in claim 27 wherein the closure flap is adapted to be moved into the closure or open position pneumatically or hydraulically.

30. Apparatus as set forth in claim 1 wherein one of said two capillary side conduits is connected to said vacuum conduit.

31. Apparatus as set forth in claim 30 wherein the reduced pressure conduit is associated with a filter device of the housing block.

32. Apparatus as set forth in claim 30 wherein the side conduit for the reduced pressure or vacuum conduit is further from the metering needle than the other side conduit.

33. A method for the volumetric metering of fluid, pasty and/or powdery substances, in particular for separating small amounts of substance from a delivery flow, by means of a plurality of adjustable-volume capillary measurement chambers which are connected to feed conduits and which are provided with outlets, in particular by means of an apparatus as set forth in claim 1, wherein the components for delivery flow are metered in the capillary measurement chambers and are respectively transferred at the outlet of each of the capillary measurement chambers into receiving vessels wherein, after the metering operation, the side conduits of the apparatus are cleaned by counter-flow with the outlet of the capillary measurement chambers closed.

34. A method as set forth in claim 33 wherein the outlets of the measurement chambers are controlled individually.

35. A method as set forth in claim 33 wherein the outlets of the measurements chambers are controlled in groups.

36. A method as set forth in claim 33 wherein the outlets of the measurement chambers are controlled jointly.

* * * * *